US012672898B2

(12) United States Patent
McCallum

(10) Patent No.: US 12,672,898 B2
(45) Date of Patent: Jul. 7, 2026

(54) DEVICE FOR ASSISTANCE IN FEMALE LABOR AND METHODS OF USING SAME

(71) Applicant: Jamie McCallum, Weybridge, VT (US)

(72) Inventor: Jamie McCallum, Weybridge, VT (US)

( * ) Notice: Subject to any disclaimer, the term of this patent is extended or adjusted under 35 U.S.C. 154(b) by 516 days.

(21) Appl. No.: 18/310,117

(22) Filed: May 1, 2023

(65) Prior Publication Data

US 2024/0366266 A1     Nov. 7, 2024

Related U.S. Application Data

(63) Continuation-in-part of application No. 17/200,845, filed on Mar. 14, 2021, now Pat. No. 11,678,910.

(51) Int. Cl.
| | |
|---|---|
| *A61B 17/42* | (2006.01) |
| *A61B 17/00* | (2006.01) |
| *A61B 17/44* | (2006.01) |
| *A61B 34/00* | (2016.01) |
| *A61B 90/00* | (2016.01) |

(52) U.S. Cl.
CPC .............. *A61B 17/42* (2013.01); *A61B 34/25* (2016.02); *A61B 2017/00017* (2013.01); *A61B 2017/00544* (2013.01); *A61B 17/44* (2013.01); *A61B 2090/035* (2016.02); *A61B 2090/064* (2016.02)

(58) Field of Classification Search
CPC ......... A61B 17/42; A61B 17/44; A61B 34/25; A61B 2090/035; A61B 2090/064; A61B 2017/00017; A61B 2017/00544; A61B 2090/032; A61B 2017/00407; A61B 2017/00535; A61B 5/227; A61B 5/4431; A61B 5/442; G01N 3/08; G01N 2203/0089
See application file for complete search history.

(56) References Cited

U.S. PATENT DOCUMENTS

| | | | | |
|---|---|---|---|---|
| 718,766 | A * | 1/1903 | Ingram | .................... A61H 7/00 601/133 |
| 4,432,376 | A * | 2/1984 | Huszar | ................. A61B 5/4331 600/587 |
| 6,527,321 | B1 * | 3/2003 | Kuciauskas | ............... E01H 1/12 135/66 |
| 7,681,477 | B2 * | 3/2010 | Alexander | ................ B25B 7/10 81/413 |
| 11,185,385 | B1 * | 11/2021 | Rushing | ............. A61B 17/2833 |
| 2008/0083813 | A1 * | 4/2008 | Zemlok | ................ A61B 17/068 227/181.1 |
| 2021/0069870 | A1 * | 3/2021 | Kwon | ..................... B25B 7/126 |
| 2021/0275395 | A1 * | 9/2021 | Scrable | .................. A61H 23/00 |

OTHER PUBLICATIONS

Text version of U.S. Pat. No. 4,432,736 due to scanned missing cols. 5 and 6. (Year: 1984).*

* cited by examiner

*Primary Examiner* — Shaun L David
*Assistant Examiner* — Cherie M Poland

(57) ABSTRACT

Methods and devices are provided for the alleviation of pain during childbirth. Generally, the methods and devices are designed to apply pressure to the hips of a female during the labor process. These devices may be manually or automatically actuated to provide pressure to the hips of a patient and the devices may further include force limiting devices to ensure that excessive forces are not applied to the patient.

18 Claims, 13 Drawing Sheets

502 Select and assemble device

504 Apply device to patient and lock

506 Activate Control Module

510 Select algorithm

512 Apply force per algorithm

514 Remove device from patient

516 Remove and dispose pad covers

518 Clean device

DEVICE FOR ASSISTANCE IN FEMALE LABOR AND METHODS OF USING SAME

CROSS-REFERENCE TO RELATED APPLICATIONS

This application is a continuation in part of U.S. patent application Ser. No. 17/200,845, filed Mar. 14, 2021, now U.S. Pat. No. 11,678,910.

FIELD OF THE INVENTION

The present invention relates to devices and methods for assisting in pain management during childbirth and in particular to devices and methods for providing assistance in the performance of a double hip press procedure.

BACKGROUND

During labor, certain factors combine to cause pain, often intense pain for the mother. One of these factors is that the female pelvis is stretched by the pressure of the baby's head as it descends into the birth canal. This stretching is normal and the ligaments in this area become looser due to the hormone relaxin. The joint between the two halves of the pelvis which is connected by ligaments can therefore stretch to accommodate the baby's movement. However, during this time there can be intense pressure on the sacrum, the triangular bone in the lower back and situated between the two hip bones of the pelvis. This bone cannot stretch and the pressure on it can lead to pain for the mother. One technique used to alleviate this sacral pain is referred to as a double hip squeeze. This technique relieves the pressure associated with the stretching of the pelvis and causes the pelvis to flare out slightly. This provides a level of relief for the mother and also provides some additional room for the baby to move downward.

Current methods of employing this technique are manual. During the process the mother leans forward in any position which provides the most comfort. The person performing the hip squeeze places their hands on the mother's hip bones and the thumbs are pointed toward the spine, the hands forming a "W". The person performing the hip squeeze then pushes on the hip bones inwardly and upwardly towards the mother's body and her shoulders.

In general, the harder the person performing the procedure squeezes the hips of the mother, the more relief from pain the mother feels. Because of this, the process can be quite physical for the person performing the procedure and can tire the person performing it significantly. In many cases it is recommended that two people alternate to perform the procedure so that each has an opportunity to rest and not become so physically depleted that they cannot perform the procedure effectively.

Because of the highly physical nature of the manual procedure it is desired to develop techniques, devices and procedures that reduce the workload on the person performing the procedure and that automate the procedure.

Several devices and methods have been developed previously to aid in labor. Heidenwolf, in U.S. Pat. No. 2,597,637, the entirety of which is incorporated by reference, describes an obstetrical apparatus that includes a belt with an inflatable bladder that is secured around the abdomen of a parturient woman. The belt is positioned such that inflation of the bladder applies pressure toward the belly between the hips and bottom of the uterus of the woman. The belt is held in place by a strap that is secured to the upper thigh of the woman.

Other devices have also been developed to aid with recurring back pain. Sebastian et al., in U.S. Pat. No. 4,836,194, the entirety of which is incorporated by reference, describes a therapeutic device for application to the lumbar spine. The device follows the contours of the iliac crests and overlies the sacrum and sacroiliac joints, as well as anchors below the posterior superior iliac spines of the human body. The appliance includes an external shell to extend around the abdominal region of the body with fasteners at opposite ends of the shell and an air bladder on the shell. The air bladder has a number of air chambers, including elongated air chambers which extend transversely to the longitudinal direction of the shell with lower ends shaped to lie above the iliac crests. The device includes a lower longitudinally extending air chamber and an anchoring air chamber between the longitudinally extending air chamber and the outer edge of the bladder. The anchoring air chamber extends from a central portion of the air bladder toward the opposite ends of the shell and is positioned to lie below the posterior superior iliac spines to prevent upward riding of the therapeutic device when it is in place on the human body and to provide support for the sacroiliac joints.

There is however still a need for easily employed devices and methods to specifically assist in relieving maternal pain related to labor and to make these methods less fatiguing on those performing them.

SUMMARY

In a primary concept, the device is disposed as a pair of pliers or tongs. The device comprises a first and a second elongated bar disposed for relative rotational movement with respect to one another. The proximal end each of the elongated bars includes a user input handle, while the distal end of each of the elongated bars includes a force applying pad. Between the proximal and distal device ends of the elongated bars is an axle hole for receiving an axle pin. When assembled, the elongated bars and the pin form a scissor joint disposed such that when the user moves the input handles toward each other the force applying pads in turn move toward each other. The elongated bars are further formed such that the length of the elongated bar proximal to the axle hole (closest to the input handles) on each of the elongated bars is longer than the length of the elongated bar distal to the axle hole (closest to the force applying pads). In this configuration the user applied force to the input handles exhibits a mechanical advantage such that the force experienced at the force applying pads is greater than the force applied at the user input handles. In use, the force applying pads are placed in an appropriate position to apply force to the hips of the patient in labor. The mechanical advantage then allows the user to apply high forces to the hips of the patient experiencing labor while keeping the forces they apply to the user input handles low enough to avoid fatigue for the user. The force applying pads may also be disposed such that their force applying surfaces are angled with respect to the closure plane of the elongated bars. In this way, as force is applied inwardly by the force applying pads it is also applied in a slightly upward manner, mimicking the manual double hip press procedure forces.

In a second, alternative embodiment, the distal and proximal lengths of the elongated bars are equal such that the force applied to the user input handles is equal to the force experienced at the hips of the patient, allowing the user to know the force the patient feels on their hips.

In a third embodiment of the device described above the axle hole is replaced with an axle slot and the axle pin is replaced with a screw and a nut that allows the user to adjust the relative difference between the distal and proximal elongated bar lengths and then tighten the nut onto the screw to maintain this relative difference in use. In this way the user can adjust the mechanical advantage the device produces to meet what is needed during the procedure.

In a fourth embodiment of the device described above, the proximal, the distal or both the proximal and distal portions of the elongated bar are disposed such that the bar will deflect at a predetermined force, ensuring that the force applied to the hips of the patient in labor does not exceed a predetermined value. In an alternative, spring loaded or ratcheted force devices are also contemplated.

In all of the embodiments above, the distal portion of the elongated bar may include one or more bends such that the distal portion of the elongated bar provides clearance between the patient in labor and the main portion of the elongated bar that extends toward the axle or other pivot point. In a like fashion the proximal end of the elongated bars may include one or more bends disposed such that the user input handles are positioned for ergonomic use by the user.

In another, fifth embodiment of the invention, the device may include a power assist. In this embodiment, an electrical, hydraulic or pneumatic system may be added to the basic scissor mechanism described above. The power assist system would be placed on the device and would comprise sensors capable of detecting the force or displacement of the user input handles and then provide a force to press the force applying pads against the patient's hips. In this embodiment, the system would include and electronic control that senses either the movement of the user input handles or the force applied to the user input handles and then applies a corresponding force to the elongated bars. This corresponding force may be the same as that input at the user input handles or a force higher or lower than that force. The control circuit may also include a force limit that prevents the power assist system from applying a force to the patient's hips greater than a predetermined force, regardless of the force applied at the user input handles. The control system may also be disposed to continually increase the force applied to the hips of the patient as long as the user is applying a closing force on the user input handles and continually decrease the force applied to the hips of the patient as long as an opening force is applied.

In a sixth embodiment, the power assist device described about may include a patient actuated control. In this embodiment, a patient actuated controller is included. This patient actuated controller may be wired to the power assist controller or may send commands to the power assist controller via infrared, radio, ultrasonic or other wireless means known in the art. In this way the patient may control the device to actively address and relieve pain that they feel. In this embodiment, a strap, belt or other means may be used to hold the force applying pads at the correct location on the body of the patient.

In yet a seventh embodiment of the present invention, control of power assist may be implemented through algorithms wherein the pressure applied to the hips of the patient cycles through a predetermined series of levels and wherein the levels may be either selected from a preset group of levels and/or programmed into the devices by a health care professional or other user.

The above-noted features and advantages of the present invention, as well as additional features and advantages, will be readily apparent to those skilled in the art upon reference to the following detailed description, accompanying drawings and appended claims, which include a disclosure of the best mode of making and using the invention presently contemplated.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

DETAILED DESCRIPTION

The present disclosure relates generally to a device for assisting in the alleviation of pain related to childbirth and more specifically elates a device for applying pressure to the hips of a female during the labor process.

It will be recognized that the scope of the present disclosure is not limited by specific applications, and that the apparatus and methods described herein may be employed in a variety of implementations. Further, while the ensuing disclosure includes illustrative embodiments employing mechanisms for applying pressure to the hips of a patient, it will be appreciated that the disclosure contemplates the use of the device on other body parts where pressure applied to those body parts performs a therapeutic function.

Figure 1:
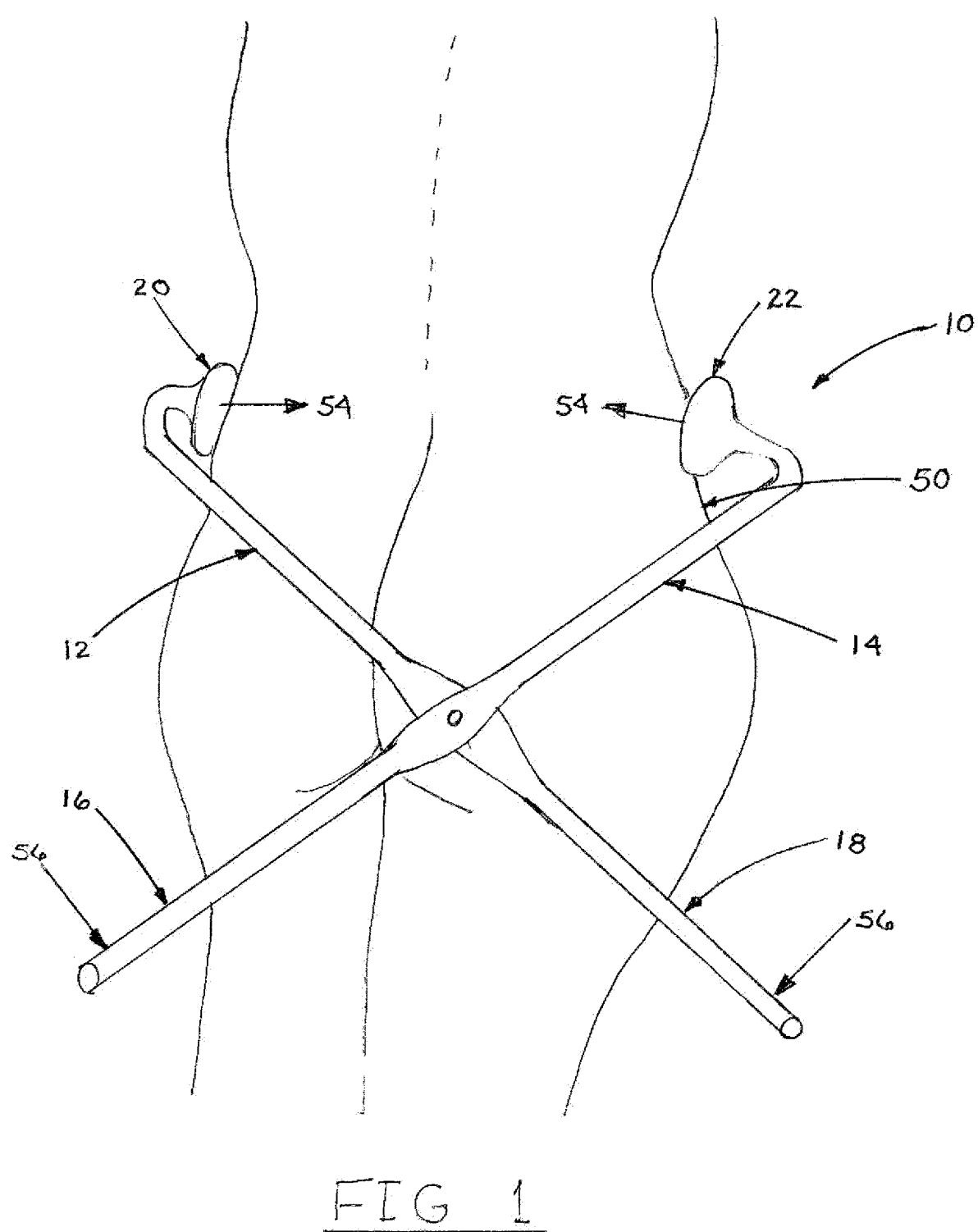
FIG. 1 is a view of the double hip pressure device on the hips of a person.
Figure 2:
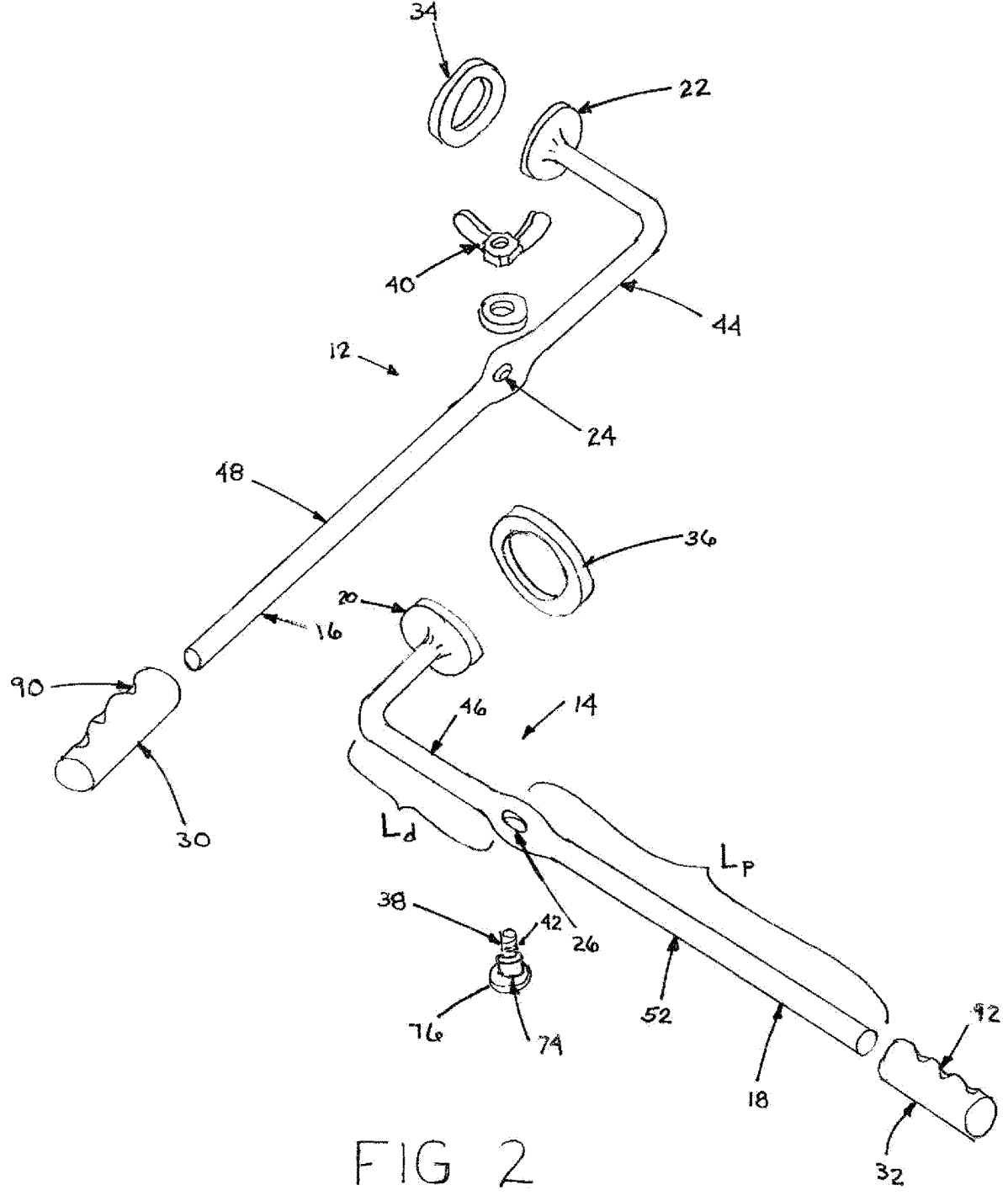
FIG. 2 is an exploded view of the double hip pressure device of FIG. 1 with a fixed mechanical advantage.

Referring to FIG. 1 and FIG. 2, a double hip pressure device 10 against hips 50 of a patient is shown. The double hip pressure device 10 comprises a first elongated bar 12 and a second elongated bar 14. The elongated bars 12 and 14 comprise user input handles 16 and 18, force applying pads 20 and 22 and axle holes 24 and 26. The user input handles 16 and 18 may include handles grips 30 and 32 and the force applying pads 20 and 22 may include covers 34 and 36. Covers 34 and 36 may be formed of a foam, rubber, leather or other materials known in the art such that the covers 34 and 36 provide a soft surface for placement against the patient's hips 50. Additionally covers 34 and 36 may be permanently fixed to force applying pads 20 and 22 or may be removeable. Covers 34 and 36 may be designed for single patient use or may designed to be cleanable for reuse. Double hip pressure device 10 further comprises an axle pin 38. Axle pin 38 is disposed to fit into axle holes 24 and 26. Axle pin 38 may be a single round pin riveted to first elongated bar 12 and second elongated bar 14 or may comprise a plurality of components such as a nut 40 and a pivot screw 42. Other attachment means know in the art are also contemplated. To create mechanical advantage in the double hip pressure device 10, the distal bar ends 44 and 46 of elongated bars 12 and 14 are shorter that the proximal bar ends 48 and 52 of elongated bars 12 and 14. The mechanical advantage of the double hip pressure device 10 is equal to the length Lp divided by the length Ld such that the output force 54 on the force applying pads 20 and 22 is equal to the input force 56 on the input handles 16 and 18 multiplied by the mechanical advantage. Force applying pads 20 and 22 oppose one another and user input handles 16 and 18 oppose one another. When the device is in an open position user input handles are disposed at a first distance relative to one another. When the device is placed on the hips 50 of the person, user input handles 16 and 18 are disposed at a second distance relative to one another where the second relative distance is less than the first relative distance. The scissor like design of double hip pressure device 10 ensures that moving the user input handles 16 and 18 away from one another also causes force applying pads 20 and 22 to move away from one another.

Figure 3A:
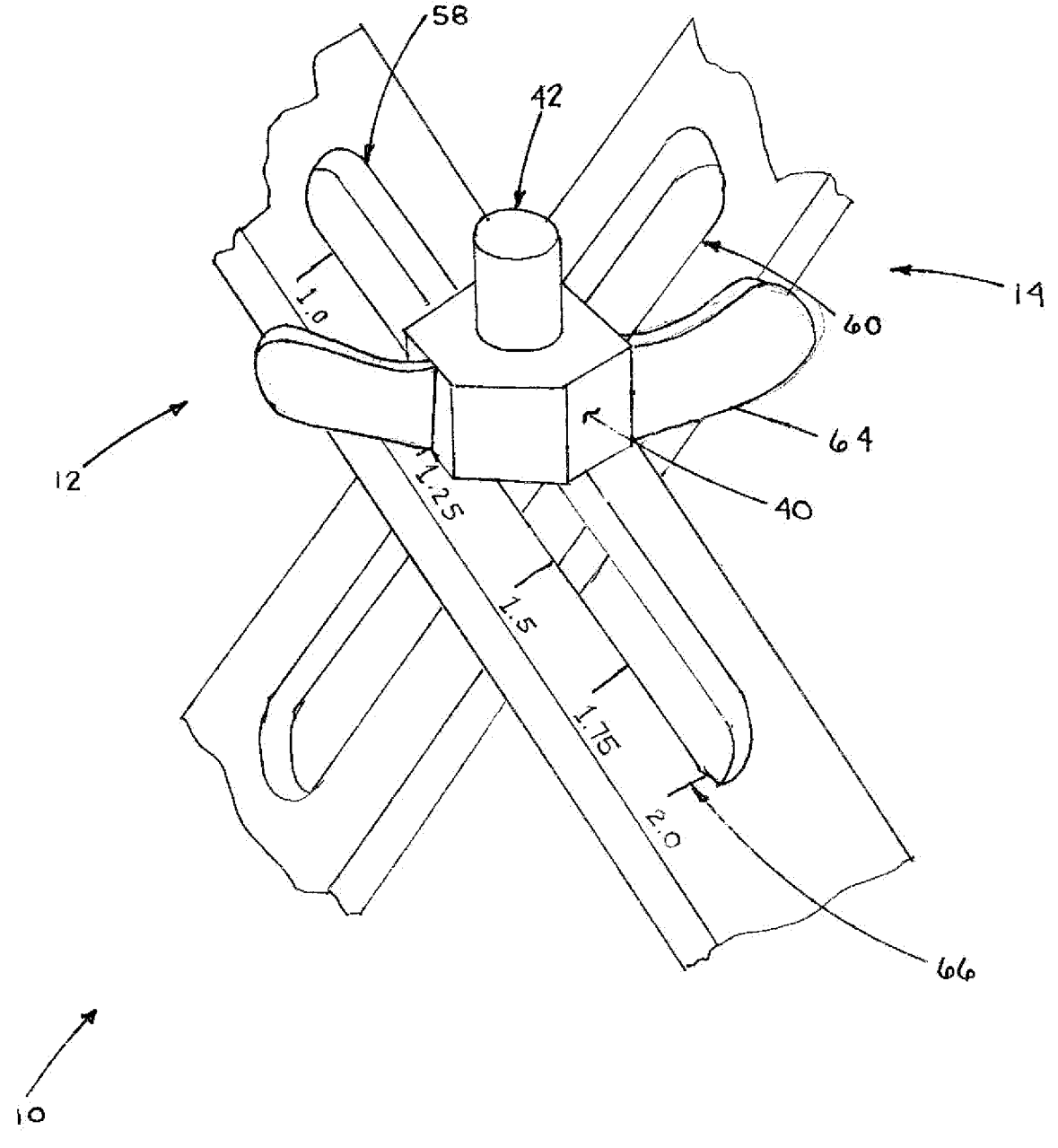
FIG. 3A is a detail view of the mechanical advantage adjustment portion of the double hip pressure device of FIG. 1. with adjustment marks.
Figure 3B:
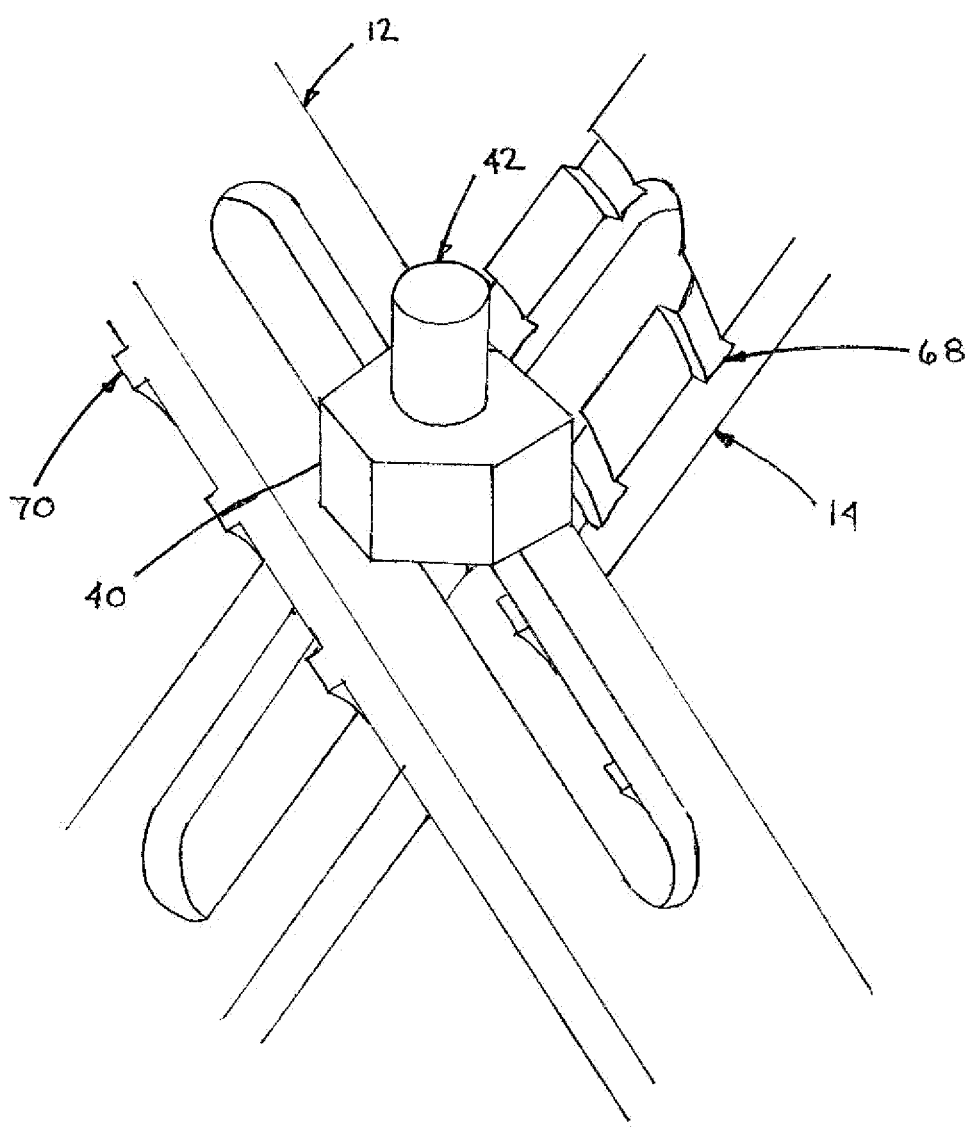
FIG. 3B is a detail view of the mechanical advantage adjustment portion of the double hip pressure device of FIG. 1 with discrete radial mechanical advantage adjustment protrusions and recesses.
Figure 3C:
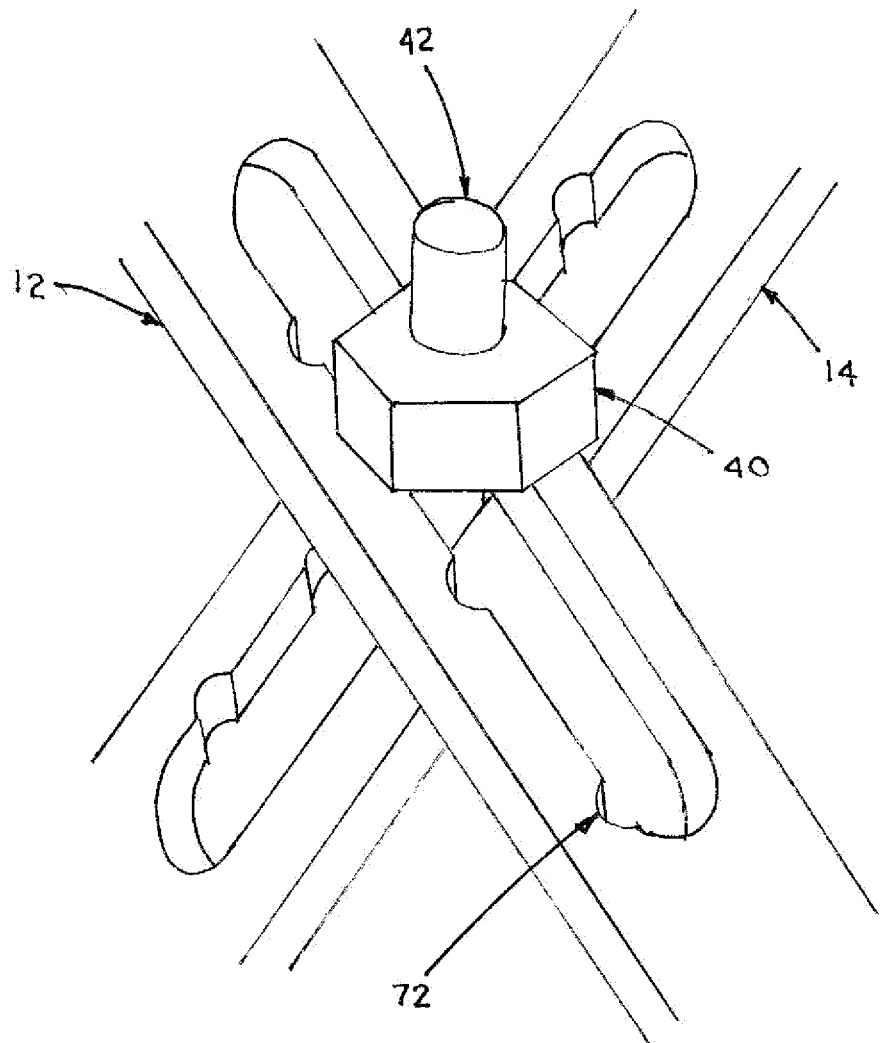
FIG. 3C is a detail view of the mechanical advantage adjustment portion of the double hip pressure device of FIG. 1 with discrete mechanical advantage adjustment slot recesses.
Figure 3D:
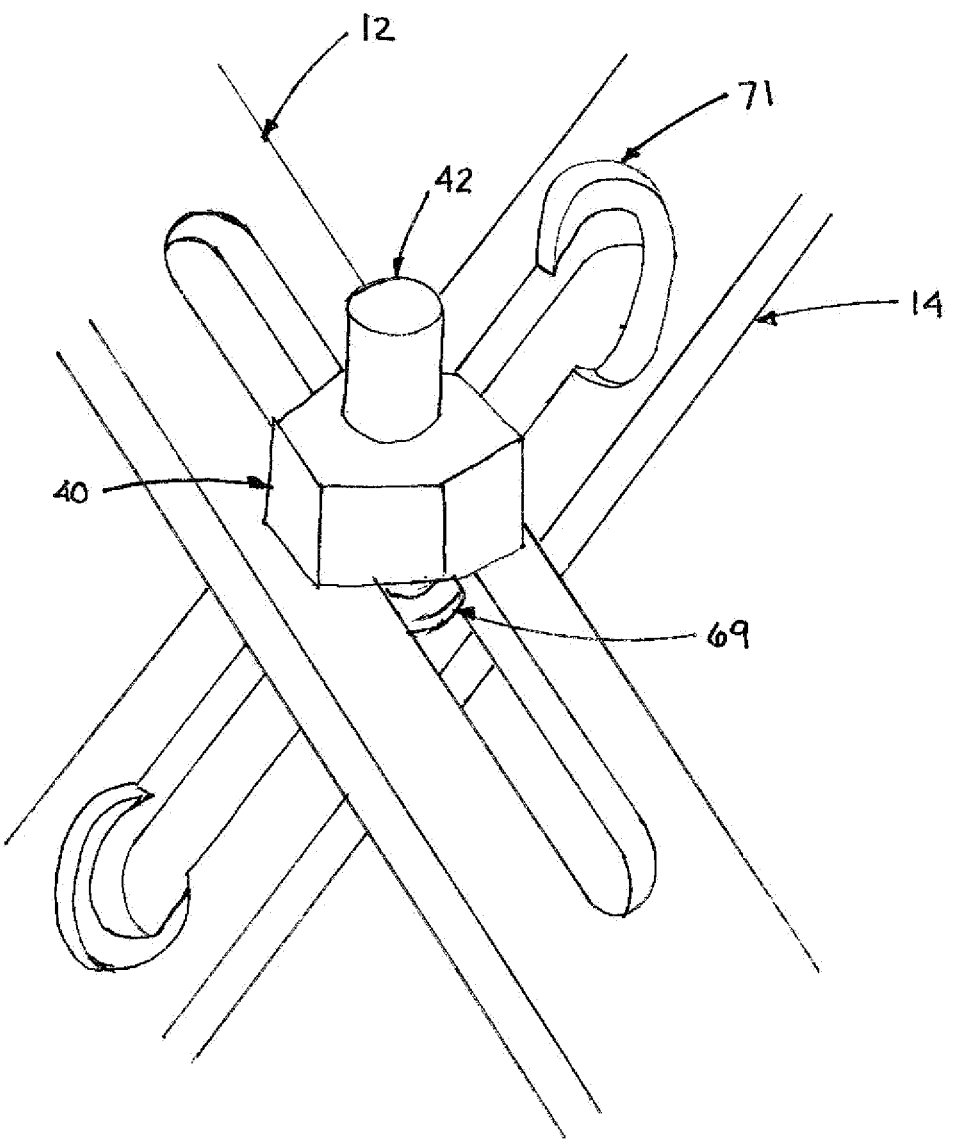
FIG. 3D is a detail view of the mechanical advantage adjustment portion of the double hip pressure device of FIG. 1 with discrete mechanical advantage adjustment rotational bearing recesses and a bearing washer.

Referring now to FIG. 3A, an alternative embodiment of double hip pressure device 10 is shown. In this embodiment first elongated bar 12 of double hip pressure device 10 includes a first axle slot 58 and second elongated bar 14 includes a second axle slot 60. In an alternative embodiment axle slot 58 is a hole. The assembly of double hip pressure device 10 further comprises a pivot screw 42 and a nut 40. The device may also include a bar (not shown) which is disposed to maintain the length Lp on the first elongated bar 12 to be equal to the length Lp on the second elongated bar 14 so that the distance from the pivot screw 42 to the force applying pads 20 and 22 of the first elongated bar 12 and the second elongated bar 14 are equal. Nut 40 may include finger tightening projections 64 or may require a tool to loosen or tighten nut 40 onto screw 42. In use, the user loosens nut 40 and adjusts the relative length Ld with respect to length Lp, thereby adjusting the mechanical advantage of the double hip pressure device 10. Elongated bars 12 and 14 may further comprise a series of marks 66 on the elongated bars 12 and 14 adjacent to axle slots 58 and 60 where the marks 66 indicate numerically the amount of mechanical advantage when the pivot screw 42 is set at one of the series of marks 66. Referring to FIG. 3B. the elongated bars 12 and 14 may further comprise interlocking recesses 68 and protrusions 70 at specified locations on the elongated bars 12 and 14 at locations concurrent with specific levels of mechanical advantage. In an alternative embodiment shown in FIG. 3D, both elongated bars 12 and 14 include recesses 71 and a pivot washer 69 is disposed in the recesses. In another alternative embodiment which is not shown, elongated bars 12 and 14 include a series of discrete holes at a predetermined spacing two of which the pivot screw 42 is disposed within to set the mechanical advantage of the double hip pressure device 10. In yet another alternative embodiment shown in FIG. 3C the slots include indentations 72 to hold pivot screw 42 in a specified position. The user slides the elongated bars 12 and 14 to set the mechanical advantage and then tightens the nut 40 onto the screw 42. Screw 42 includes a step 74 that the nut 40 tightens against and the length of screw 42 from the base of the screw head 76 to the step 74 is disposed such that the screw 42 and nut 40 hold the first elongated bar 12 and the second elongated bar 14 in close proximity without causing frictional binding between them. The double hip pressure device 10 may further comprise a wave spring (128) that when assembled is disposed over the pivot screw 42 and between the nut 40 and one of elongated bars 12 and 14. The wave spring 128 is disposed to eliminate any slack between the nut 40 and one of the elongate bars 12 and 14 such that the opening and closing motion of elongate bars 12 and 14 does not feel loose but also does not bind to prevent their free motion.

Figure 4:
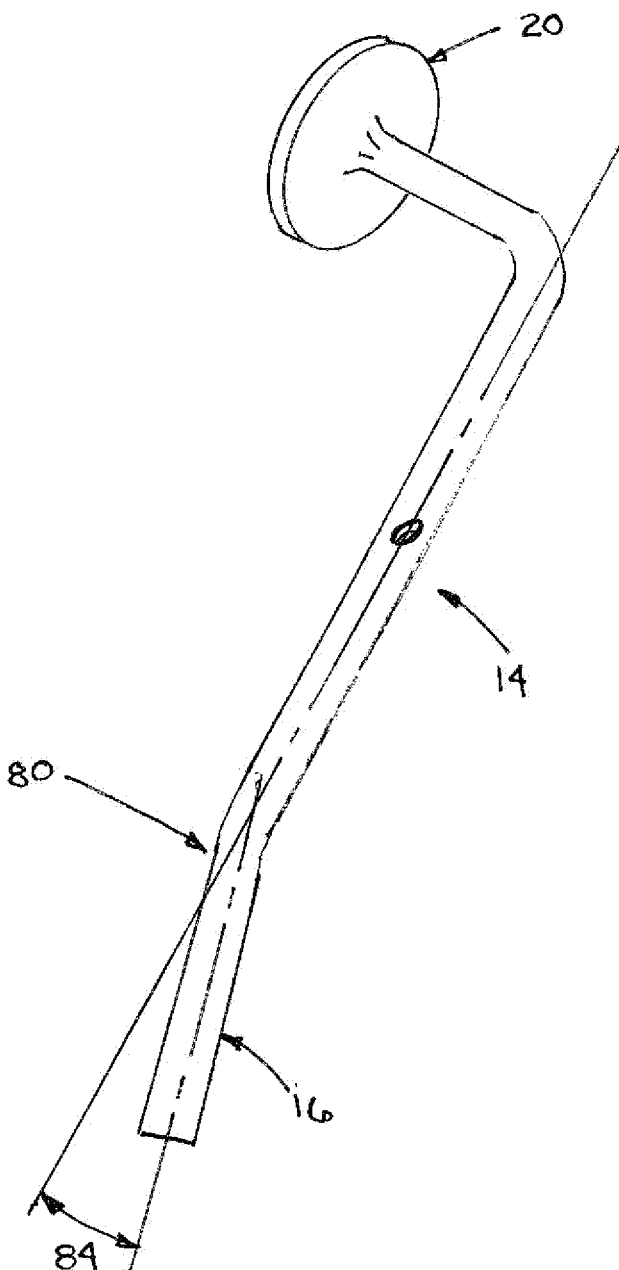
FIG. 4 is a detail view of an elongated bar of the double hip pressure device of FIG. 1 with handles which are ergonomically bent.

Referring now to FIG. 4, which shows a version of elongated bar 12 (however elongated bar 14 would exhibit like characteristics), the user input handles 16 and 18 are disposed at the distal end of first elongated bar 12 and second elongated bar 14 respectively. In an embodiment not shown, the user input handles 16 and 18 are simply a continuation of ends of the elongated bars 12 and 14 and extend along the same axis as the elongated bars 12 and 14. In a preferred embodiment shown in FIG. 4, the user input handles 16 are disposed at the end of bent portions 80. Bent portions 80 are disposed at angles 84 and extend at angles 84 off of the axis of elongated bars 12 respectively. Angles 84 are preferentially equal and are disposed such that when double hip pressure device 10 is placed on the patient the user input handles are positioned such that the user has the best ergonomic position for applying forces to the handles. As mentioned previously, user input handles 16 and 18 are covered by handle grips 30 and 32 respectively. Handle grips 30 and 32 may be formed of resilient materials such as open or closed cell foams, silicone or other rubber materials or other resilient materials known in the art. Handle grips 30 and 32 may include finger recesses 90 and 92 or may be disposed with one or more finger holes (not shown) to improve gripping of the handle grips 30 and 32. Handle grips 30 and 32 may also include a combination of finger recesses and finger holes. In a like way, the distal ends of elongated bars 12 and 14 may include bends (not shown) proximal to the force applying pads 20 and 22. In this way, there is additional clearance between the person's hips 50 and the device proximal to the force applying pads 20 and 22.

Figures 5A, 5B, 5C:
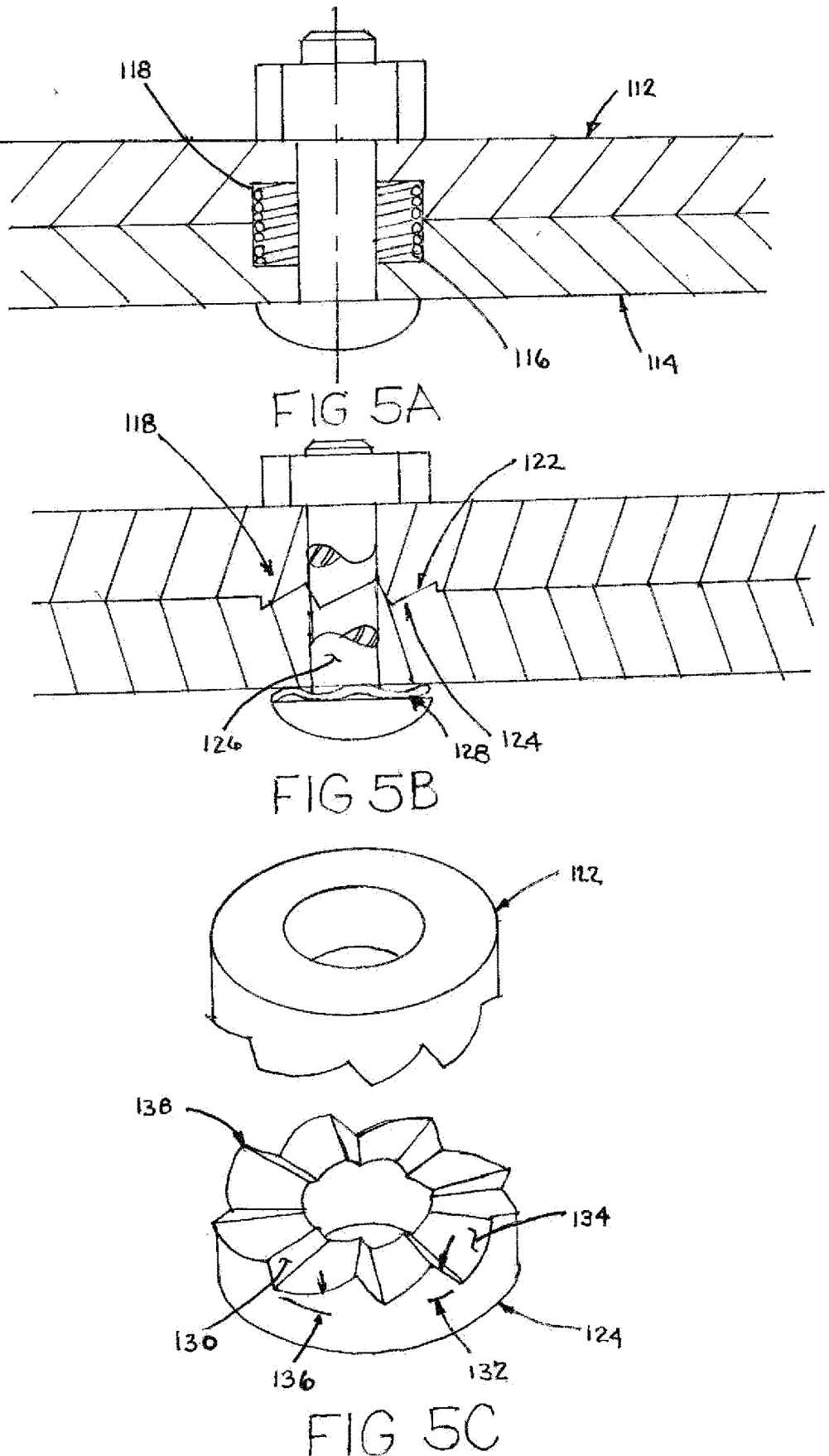
FIG. 5A is a detail view of the joint of a force limited double hip pressure device utilizing a torsional spring.
FIG. 5B is a detail view of the joint of a force limited double hip pressure device utilizing a ratcheting mechanism.
FIG. 5C is a detail view of the ratchet surfaces of the ratchet mechanism of FIG. 5B.

Referring now to FIGS. 5A-5C, a force limited bar 112 is shown. Force limited bar 112 is similar to elongated bar 12 of FIG. 1 but also includes a force limiting portion 114. Force limiting portion 114 is disposed such that it deflects at a predetermined force. Various embodiments can provide for the deflection at a predetermined force. In one embodiment, shown in FIG. 5A, a torsional spring 116 is placed at a joint 118 of force limited portion 114. In this embodiment the elongated bar 12 is separated into two halves 112a and 112b. A torsional spring 116 is placed between elongated bar halves 112a and 112b such that the two halves may move relative to one another. Torsional spring 116 is preloaded to a predetermined value such that it does not deflect until a predetermined force is applied to force applying pad 120. The spring constant of torsional spring 116 may be selected such that once the predetermined force on force applying pad 120 is reached, the torsional spring 116 deflects rotationally for large displacements without a significant change in the torque that torsional spring 116 produces. In this way the force limit on force limited bar 112 is nearly constant.

In a second embodiment of the force limited concept, shown in FIGS. 5B and 5C, elongated bar 112 is again split into halves 112a and 112b and joint 118 comprises a first ratcheted half 122 and a second ratcheted half 124 a ratchet pin 126 a wave spring 128 and the torsional spring 116. First ratcheted half 122 and second ratcheted half 124 have a first ratcheted surface 130 which is disposed at a first ratchet angle 132 and second ratcheted surface 134 is disposed at a second ratchet angle 136. In this embodiment ratchet spring 128 pushes first ratcheted half 122 against second ratcheted half 124. As force is applied to force limited bar 112 first ratcheted surface 130 of first ratcheted half 122 is driven against first ratcheted surface 130 of second ratcheted half 124. As the force applied to force limited bar 112 increases, first ratcheted half 122 slides relative to second ratcheted half along first ratchet angle 132. This relative motion compresses wave spring 128 and causes the joint 118 to keep the ratchet surfaces in contact and maintain a torsional force at a predetermined value until the first ratcheted surface 130 of first ratcheted half 122 reaches the top 138 of first ratcheted surface 130 of second ratcheted half 124. At this point the second ratcheted surface 134 of both first ratcheted half 122 and second ratcheted half 124 come in contact and the first ratcheted half 122 moves relatively freely with respect to second ratcheted half 124 until the next first ratcheted surface 130 of first ratcheted half 122 comes into contact with the next first ratcheted surface 130 of second ratcheted half 124 and the force limit is again introduced. The user then can open the device, overcoming the force from second ratcheted surface 134. First ratchet angle 132 is larger than second ratchet angle 136 so that when force is removed from the force limited bar 112, the torsional spring 116 has sufficient torsion to overcome the torsional force created by the second ratcheted surface 134 and place the joint 118 of force limited bar 112 in its original position. In an alternative embodiment, the torsional spring 116 and the ratcheted surfaces 130 and 134 are combined such that when the user removes force from the force limited bar 112, the torsional spring 116 provides a torque greater than that required to overcome the torque on the ratcheted surface 134 such that the device opens without the user having to supply force on their own to initiate the opening.

Figure 5D:
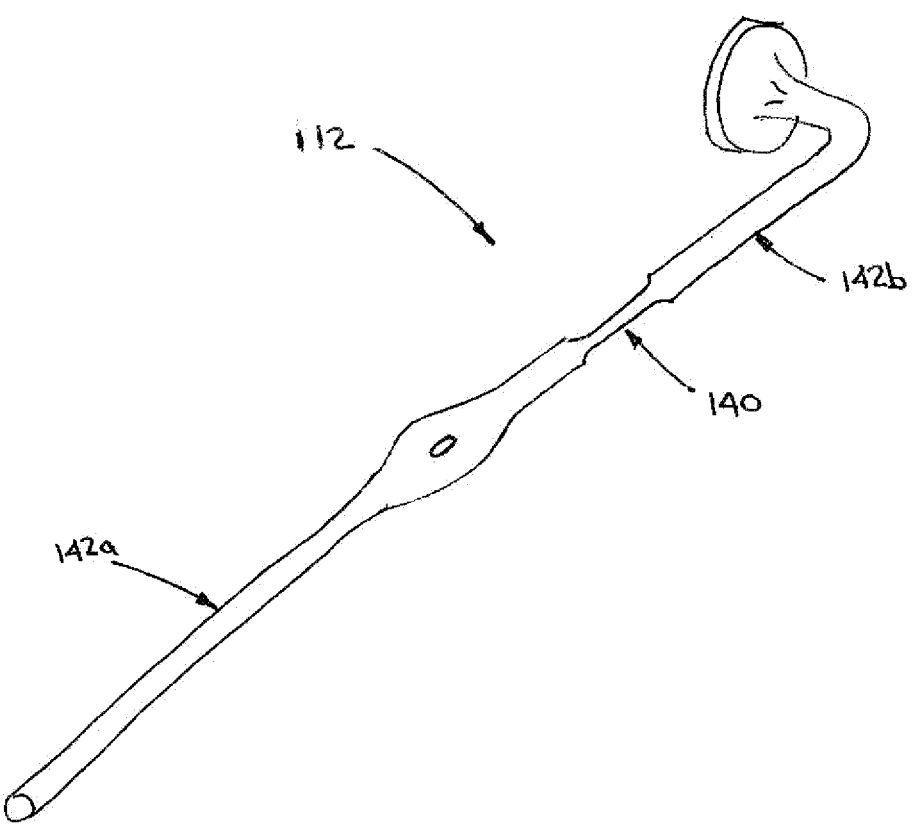
FIG. 5D is a detail view of the elongated bar of a force limited double hip pressure device utilizing a deflecting bar section.

In yet another embodiment of a force limiting design as shown in FIG. 5D, the force limited bar 112 includes a first cross-sectional area 140 and a second cross sectional area 142a and 142b. First cross-sectional area is disposed along the distal portion of force limited bar 112 while second cross sectional area 142 is used over the remainder of the force limited bar 112. First cross sectional area 140 may have a smaller cross section that second cross sectional area 142 such that cross sectional area 140 elastically deflects at a predetermined force while second cross sectional area 142a and 142b remains substantially rigid when exposed to the same force.

It is also contemplated that other force limiting designs such as over-center mechanisms, frictional mechanisms or other mechanisms known in the art may be used. While shown as separate embodiments, it is contemplated that all the force limiting embodiments described above may be used independently or in any combination.

Figure 6:
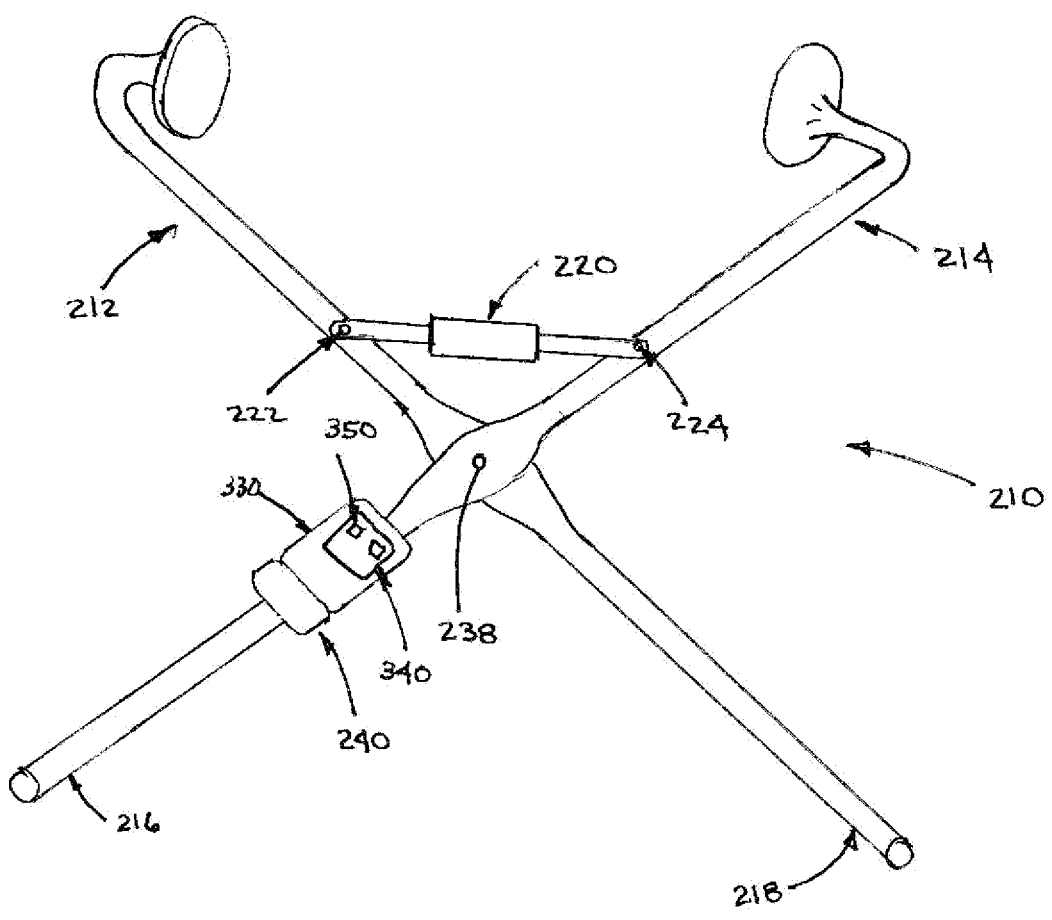
FIG. 6 is a view of a power assisted double hip pressure device with extended handles.

While manual mechanisms have been described above, other power assisted and/or automated embodiments may also be employed. Referring to FIG. 6, a power assist double hip pressure device 210 is shown. In this embodiment, first elongated bar 212 and second elongated bar 214 are connected with axle pin 238. Proximal or distal to axle pin 238 is power assist piston 220. Power assist piston 220 includes a sensor (240) that detects when a user is applying pressure to the first elongated bar 212 and/or the second elongated bar 214. When the sensor detects that the user is applying pressure to close the double hip pressure device 210 at user input handles 216 and 218, the power assist piston 220 exerts a closure force on the first elongated bar 212 and the second elongated bar 214 at pin connections 222 and 224 respectively. In a like fashion, when the sensor detects that the user is applying pressure to open the double hip pressure device 210, the power assist piston 220 exerts an opening force on the first elongated bar 212 and the second elongated bar 214 at pin connections 222 and 224 respectively. The power assist piston 220 may be designed such that the opening and closing forces are equal or inequal and that the speed at which the opening and closing of the double hip pressure device 210 is performed is equal or inequal. The power assist piston 220 may be a hydraulic piston, a pneumatic piston a solenoid piston or other piston architecture known in the art. The double hip pressure device 210 may further comprise a battery (not shown) that powers the power assist piston 220 and may also further comprise a pneumatic or hydraulic motor (not shown) that supplies the required fluid under pressure to actuate the power assist piston 220.

Alternatively, the electricity or pressurized fluids that power the power assist piston 220 may be provided by a source external to the double hip pressure device 210.

Figure 7:
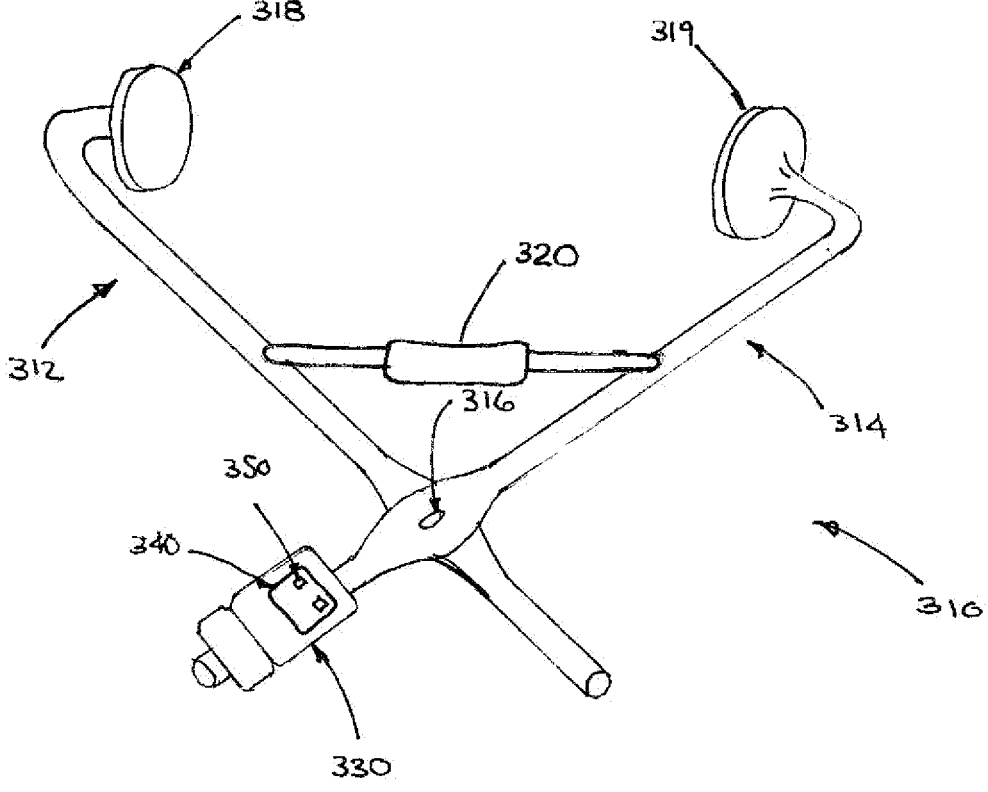
FIG. 7 is a view of an alternate embodiment of the power assist device with truncated handles.

Referring now to FIG. 7, another embodiment of a double hip pressure device 310 is shown. In this embodiment, the double hip pressure device 310 comprises a first elongated bar 312, a second elongated bar 314, a pivot axle 316 force applying pads 318 and 319, a power assist piston 320 and a controller 330. In a preferred embodiment of the design in FIG. 7, the proximal portions of the first elongated bar 312 and the second elongated bar 314 are shorter than other designs shown in other figures herein. In this design, the force applying pads 318 and 319 are placed against the hips of the patient. A frictional locking mechanism (not shown) may be employed to hold them in place until the double hip pressure device 310 can be activated. When the double hip pressure device 310 is activated, the power assist piston 320 applies pressure applied to the hips of the patient through the pressure applying pads 318 and 319. The controller 330 determines the pressure that the power assist piston 320 provides through a pre-programmed algorithm or in an alternative embodiment, a user console 340 is connected to the controller 330 so that a user can select specific algorithms for the controller 330 to run or can directly control the controller 330 to select specific pressures to be applied. The controller 330 may include a memory (not shown) and a processor (not shown) or may alternatively include an application specific integrated circuit (ASIC) for providing the control signals to the power assist piston 320. In one embodiment of an algorithm, the controller 330 causes the piston 320 to apply a force necessary for the force applying pads 318 and 319 to apply a force to hips 50 that is a multiple of the force applied to the handles. In addition, the indicated multiple may be a value that the user inputs into user console 340. In an alternative embodiment, user console 340 includes at least one user input control(s) 350 which permits the user to select from a plurality of preprogrammed algorithms for the application of force. User console 340 may also include an output screen (not shown) that displays the selected algorithm or that displays a list of algorithms for the user to choose with the user input control(s) 350. User input control(s) 350 may also allow the user to input information related to the patient being treated or other information. User input controls may take the form of a keypad, a dial a joystick or any other input device known in the art. The user console 340 may include wireless or wired communication to either download from another device, computer server or similar electronic device software updates, user profiles, applications, algorithms or other information or to upload onto another device, computer server or similar electronic device, patient information, treatment information, device status or other similar information.

In an alternative embodiment to the double hip pressure device 10 of FIG. 6 and FIG. 7, the handles 216 and 218 may comprise a telescoping design wherein the proximal potion of the handle nests inside the more distal portion. In this way the device is disposed such that the user can switch between the more automated version of the design shown in FIG. 7 and the more manual version of the design shown in FIG. 6.

Figure 8:
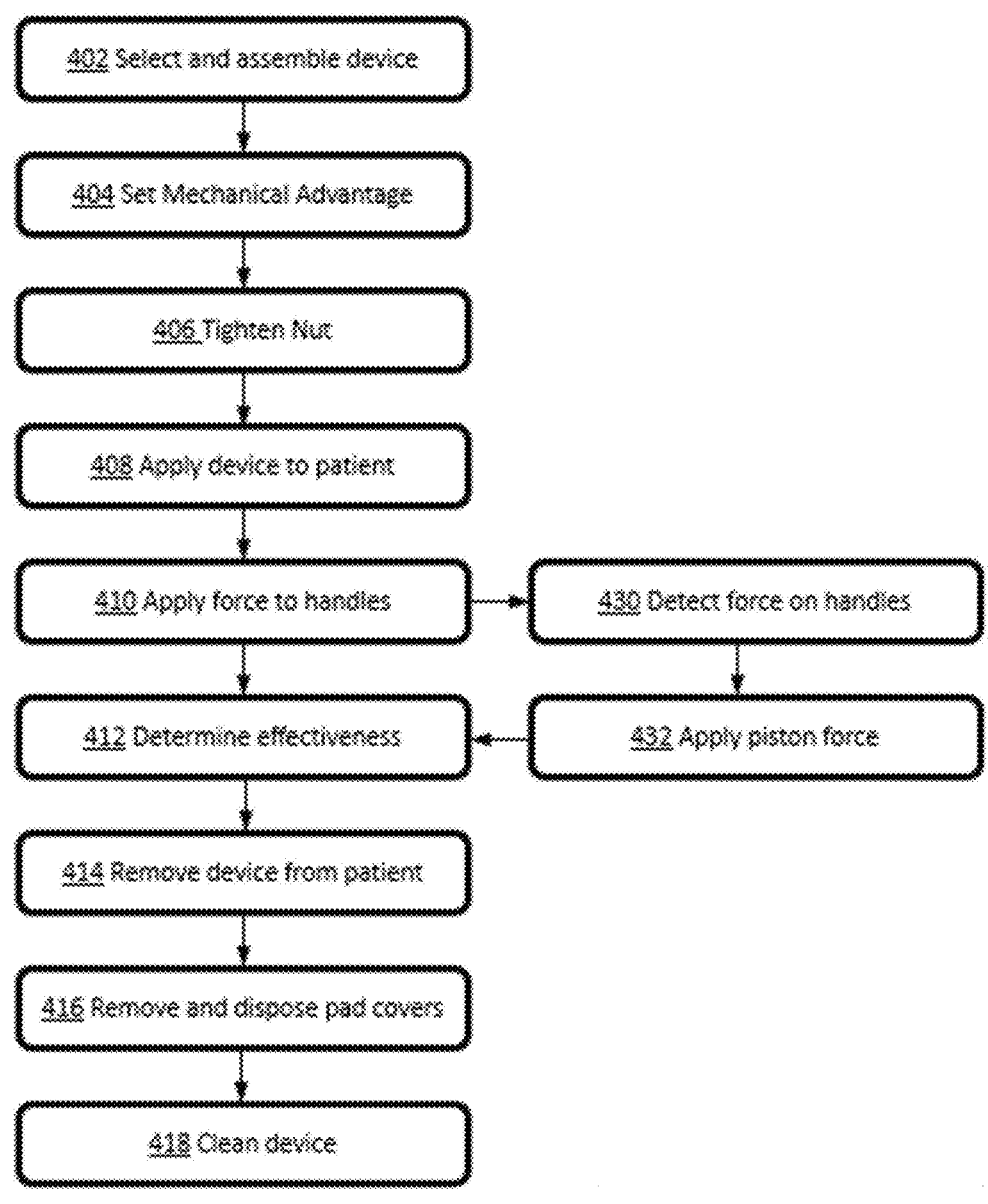
FIG. 8 is a flowchart of the steps for use of a manual double hip pressure device.

Referring now to FIG. 8 a flowchart is shown for a manual method 400 of using the double hip pressure device described above. In step 402, the double hip pressure device is selected and assembled. In step 404, the mechanical advantage of the double hip pressure device is set. In step 406, the nut on the double hip pressure device is tightened to lock the selected mechanical advantage into the device. In step 408, the user applies the double hip pressure device to the hips of the patient. In step 410, the user applies pressure to the input handles of the double hip pressure device. In optional step 430 a sensor detects the pressure put on the input handles and augments the pressure applied with a power assist delivered by a power assist piston like that described above. In step 412, the user determines the effectiveness of the pressure applied in step 410 and either increases or decreases the pressure as appropriate. Step 412 can be repeated multiple times throughout the labor as needed to relieve the labor pains of the patient. In step 414 the double hip pressure device is removed from the patient and disassembled. In optional step 416 the pads are removed and disposed. In step 418 the double hip pressure device is cleaned. Cleaning may be performed with simple disinfecting agents or the device may be steam sterilized.

Figure 9:
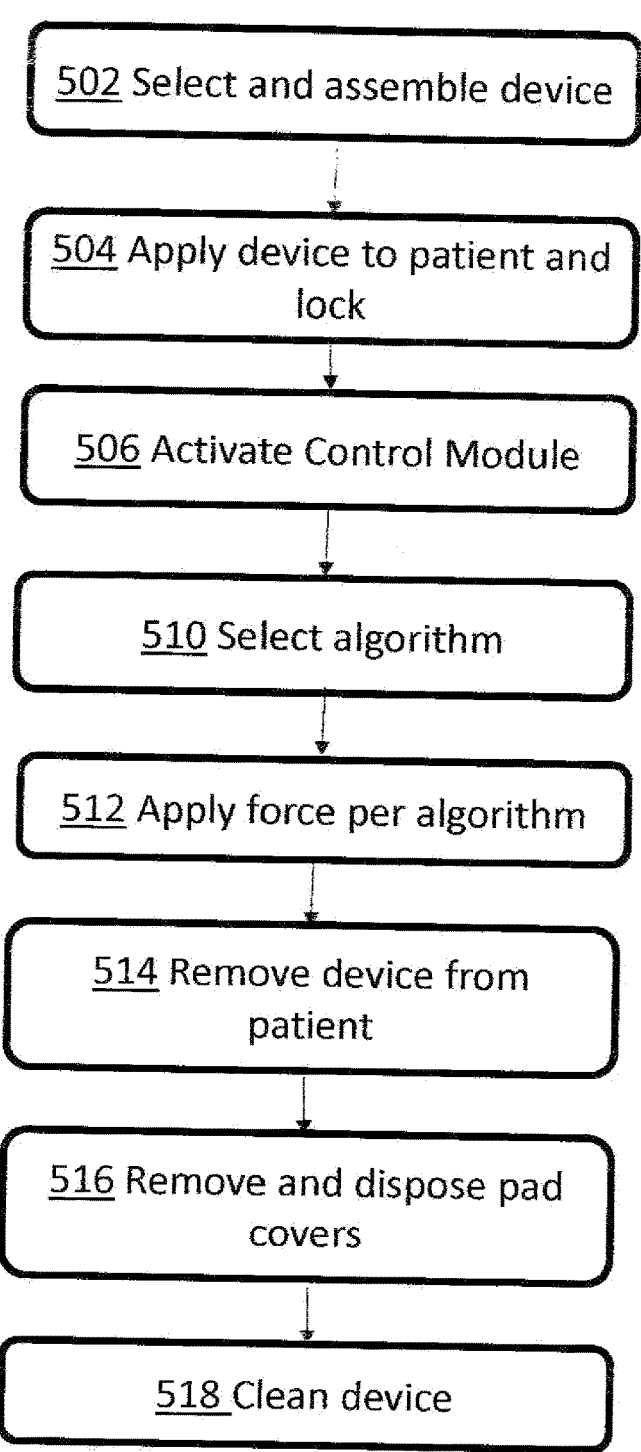
FIG. 9 is a flowchart of the steps for use of an automated double hip pressure device.

Referring now to FIG. 9 a flowchart is shown for a fully automated method 500 of using the double hip pressure device shown in FIG. 7. In step 502, the double hip pressure device is selected and assembled. In step 504, the user applies the double hip pressure device to the hips of the patient and locks it in place. In step 506, the user activates the controller module of the automated double hip pressure device. In optional step 510 the user selects an algorithm from a plurality of algorithms for use with the double hip pressure device from a user interface on the controller. In step 512, the controller of the double hip pressure device applies the selected algorithm to apply pressure per the algorithm to the hips of the patient. In step 514 the double hip pressure device is removed from the patient and disassembled. In optional step 516 the pads are removed and disposed. In step 518 the double hip pressure device is cleaned. Cleaning may be performed with simple disinfecting agents or the device may be steam sterilized.

While the disclosure has been described herein in reference to specific aspects, features and illustrative embodiments, it will be appreciated that the utility of the disclosure is not limited, but rather extends to and encompasses numerous other variations, modifications and alternative embodiments, as will suggest themselves to those of ordinary skill in the field of the present disclosure, based on the description. Correspondingly, the invention as claimed is intended to be broadly construed and interpreted, as including all such variations, modifications and alternative embodiments, within its spirit and scope.

I claim:

1. A device for assistance in female birth labor, comprising;
a first elongated bar, comprising;
a first user input handle; and
a first force applying pad; and
a second elongated bar, comprising;
a second user input handle; and
a second force applying pad,
wherein said first user input handle opposes said second user input handle and wherein said first force applying pad opposes said second force applying pad, wherein said first force applying pad is disposed to be positioned against a first hip of a person and said second force applying pad is disposed to be positioned against a second hip of a person, wherein said first user input handle and said second user input handle have an open position, wherein said first user input handle and said second user input handle are spaced apart at a first distance and wherein said first user input handle and said second user input handle have a closed position, wherein said first user input handle and said second user input handle are spaced apart at a second distance and wherein said second distance is less than said first distance, wherein a first handle force applied to the first user input handle is transferred to said first hip of said person through said first elongated bar and a first pad force is output to said first hip at said first force applying pad such that said first pad force is proportional to said first handle force and a second handle force applied to said second user input handle is transferred to said second hip of said person through second elongated bar and a second pad force is output to said second hip at said second force applying pad such that said second pad force is proportional to said second handle force and wherein at least one of said first force applying pad and second force applying pad are angled with respect to a closure plane of said first user input handle and said second user input handle such that said first force applying pad and said second force applying pad have a first force component in said closure plane and a second force component which is perpendicular to said closure plane.

2. The device for assistance in female birth labor of claim 1, wherein said device further comprises;
an axle pin;
an axle fixator,
wherein first elongated bar further comprises;
a first axle opening;
a first proximal portion disposed between said first axle opening and said first user input handle; and
a first distal portion disposed between said first axle opening and said first force applying pad, wherein said second elongated bar further comprises;

a second axel opening;

a second proximal portion disposed between said second axle opening and said second user input handle; and a second distal portion disposed between said second axle opening and said second force applying pad, wherein said first distal portion and said second distal portion have the same length and wherein said first proximal portion and said second proximal portion have the same length and wherein said first proximal portion has a length greater than said first distal portion.

3. The device for assistance in female birth labor of claim 2, wherein said first axle opening and said second axle opening are elongated to form a first slot in said first elongated bar and a second slot in said second elongated bar and wherein said first elongated bar and second elongated bar are moveable with respect to said axle pin to change the length of said first proximal portion and said second proximal portion.

4. The device for assistance in female birth labor of claim 3, wherein said axle pin further comprises a screw and wherein said axle fixator further comprises a nut, wherein said nut is tightened to fix the position of said first elongated bar and said second elongated bar relative to said axle.

5. The device for assistance in female birth labor of claim 3, wherein said first elongated bar further comprises a plurality of markings adjacent said first slot and wherein said markings indicate the ratio of said first handle force to said first pad force.

6. The device for assistance in female birth labor of claim 3, wherein said first slot and said second slot include a plurality of recesses on one side of each of said slots and wherein said plurality of recesses are spaced apart along the axis of said slot and wherein said axle pin is sized to fit into said plurality of recesses.

7. The device for assistance in female birth labor of claim 1, further comprising;

a first pad cover; and a second pad cover; wherein said first pad cover surrounds said first force applying pad and said second pad cover surrounds said second force applying pad.

8. The device for assistance in female birth labor of claim 7, wherein said first cover and said second cover are formed of one of a closed cell foam, an open cell foam, a natural rubber, a synthetic rubber or leather.

9. The device for assistance in female birth labor of claim 7, wherein said first cover and said second cover a removeable form said first force applying pad and said second force applying pad respectively.

10. A device for assistance in female birth labor, comprising;

a first elongated bar, comprising;

a first user input handle;

a first force applying pad; and a first axle hole; and a force limiting device; and a second elongated bar, comprising;

a second user input handle;

a second force applying pad;

a second axle hole; and an axle; and an axle fixator, wherein said first user input handle opposes said second user input handle and wherein said first force applying pad opposes said second force applying pad and, wherein said first force applying pad is disposed to be positioned against a first hip of a person and said second force applying pad is disposed to be positioned against a second hip of a person, wherein said first force applying pad and said second force applying pad have an open position wherein said force applying pad and said second force applying pad are spaced apart at a first distance and where said force applying pad and said second force applying pad have a closed position, wherein said first force applying pad and said second force applying pad are spaced apart at a second distance and wherein said second distance is less than said first distance, wherein when said first force applying pad is positioned on a first hip of a person and said second force applying pad is positioned on a second hip of said person and wherein a first end of a piston assembly is connected to said first elongated bar and wherein a second end of said piston assembly is attached to said second elongated bar and wherein said force limiting device limits the force applied to said person and wherein at least one of said first force applying pad and second force applying pad are angled with respect to a closure plane of said first user input handle and said second user input handle such that said first force applying pad and said second force applying pad have a respective first force component in said closure plane and a second force component out of said closure plane.

11. The device for assistance in female birth labor of claim 10, wherein said first user input handle is also said force liming device and wherein said first user input handle deflects at a predetermined force.

12. The device for assistance in female birth labor of claim 10, wherein the distal end of said first elongated bar can rotate relative to the proximal end of said first elongated bar and wherein said distal end of said first elongated bar and said proximal end of said first elongated bar are connected with a torsional spring and wherein said torsional spring is said force limiting device.

13. The device for assistance in female birth labor of claim 10, wherein at least one of said first force applying pad and second force applying pad are angled with respect to the closure plane of said first user input handle and said second user input handle such that the user applies a single inward force to the user input handle which then applies both an inward and upward force on the hips of said person.

14. The device for assistance in female birth labor of claim 13, wherein said first user input handle is also said force liming device and wherein said first user input handle deflects at a predetermined force.

15. The device for assistance in female birth labor of claim 13, wherein the distal end of said first elongated bar can rotate relative to the proximal end of said first elongated bar and wherein said distal end of said first elongated bar and said proximal end of said first elongated bar are connected with a torsional spring and wherein said torsional spring is said force limiting device.

16. The device for assistance in female birth labor of claim 15, wherein said first force applying pad applies a first pad force to said first hip of said person and wherein said second force applying pad applies a second pad force to said second hip of said person and where in at least one of said first force and second force.

17. The device for assistance in female birth labor of claim 16, wherein said first pad force is equal to said second pad force.

18. The device for assistance in female birth labor of claim 16 wherein a user applies a first input force to said first user input handle and a second input force to said second user input handle and wherein said pad force is a multiple of said user input force.

\* \* \* \* \*